United States Patent
Chaturvedi et al.

(10) Patent No.: US 11,684,309 B2
(45) Date of Patent: Jun. 27, 2023

(54) SYSTEM AND METHOD TO ENHANCE DREAM RECALL

(71) Applicant: KONINKLIJKE PHILIPS N.V., Eindhoven (NL)

(72) Inventors: Akhil Chaturvedi, Pittsburgh, PA (US); Gary Nelson Garcia Molina, Madison, WI (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 265 days.

(21) Appl. No.: 17/115,878

(22) Filed: Dec. 9, 2020

(65) Prior Publication Data

US 2021/0169404 A1    Jun. 10, 2021

Related U.S. Application Data

(60) Provisional application No. 62/945,906, filed on Dec. 10, 2019.

(51) Int. Cl.
  *A61B 5/00* (2006.01)
  *A61B 5/377* (2021.01)

(52) U.S. Cl.
  CPC ............ *A61B 5/4806* (2013.01); *A61B 5/377* (2021.01); *A61B 2560/02* (2013.01)

(58) Field of Classification Search
  CPC ............ A61M 21/00–02; A61B 5/4806–4815
  See application file for complete search history.

(56) References Cited

U.S. PATENT DOCUMENTS

| | | |
|---|---|---|
| 4,735,199 A | 4/1988 | Dilullo |
| 5,551,879 A | 9/1996 | Raynie et al. |
| 2004/0266659 A1 | 12/2004 | Laberge |
| 2014/0221779 A1 | 8/2014 | Schoonover |

(Continued)

FOREIGN PATENT DOCUMENTS

| | | |
|---|---|---|
| WO | 2016005870 A1 | 1/2016 |
| WO | 2016064932 A1 | 4/2016 |

(Continued)

OTHER PUBLICATIONS

"Recurrent Deep Neural Networks for Real-Time Sleep Stage Classification From Single Channel EEG." Frontiers in Computational Neuroscience. Bresch, E., Großekathöfer, U., and Garcia-Molina, G. (2018).

(Continued)

*Primary Examiner* — Thaddeus B Cox (57) ABSTRACT

The present disclosure pertains to delivering sensory stimulation to a subject during a sleep session in order to enhance dream recall. The system may detect REM sleep in the subject during a sleep session based on brain activity of the subject. The system may then deliver sensory stimulation to the subject during the sleep session. The system may deliver sensory stimulation at a frequency in a theta range of an EEG signal in order to increase theta power in the brain activity of the subject. In some embodiments, the system may modulate the intensity of the sensory stimulation according to changes in the EEG theta power associated with the subject during the sleep session. In some embodiments, an increase in EEG theta power associated with the subject may promote dream recall.

14 Claims, 5 Drawing Sheets

500

502 — Generate output signals conveying information related to brain activity of the subject during the sleep session 504 — Detect, based on the output signals, sleep in the subject during the sleep session 506 — Control the one or more sensory stimulators to deliver sensory stimulation to the subject during the sleep session to enhance dream recall in the subject (56) References Cited

U.S. PATENT DOCUMENTS

| | | | |
|---|---|---|---|
| 2019/0070386 A1* | 3/2019 | Raut | A61B 5/4812 |
| 2019/0143073 A1* | 5/2019 | Grossman | G16H 10/00 |
| | | | 600/28 |
| 2019/0298967 A1* | 10/2019 | Garcia Molina | A61M 21/02 |
| 2020/0086078 A1* | 3/2020 | Poltorak | A61N 1/36025 |
| 2020/0139112 A1* | 5/2020 | Aharonovitch | A61B 5/4812 |

FOREIGN PATENT DOCUMENTS

| | | |
|---|---|---|
| WO | 2018051354 A1 | 3/2018 |
| WO | WO-2020153584 A1 * | 7/2020 |

OTHER PUBLICATIONS

Bellesi, M., Riedner, B. A., Garcia-Molina, G., Garcia-Molina, G., Cirelli, C., & Tononi, G. (2014). Enhancement of sleep slow waves: underlying mechanisms and practical consequences. Frontiers in Systems Neuroscience, 8, 208-208.

Marzano, C., Ferrara, M., Mauro, F., Moroni, F., Gorgoni, M., Tempesta, D., . . . Gennaro, L. D. (2011). Recalling and Forgetting Dreams: Theta and Alpha Oscillations during Sleep Predict Subsequent Dream Recall. The Journal of Neuroscience, 31(18), 6674-6683.

Reed, H. (1978). Improved dream recall associated with meditation. Journal of Clinical Psychology, 34(1), 150-156.

Schredl, M. (1995). Creativity and Dream Recall. Journal of Creative Behavior, 29(1), 16-24.

International Search Report and Written Opinion, International Application No. PCT/EP2020/084210, dated Mar. 4, 2021.

Cipollo, C. et al., "Beyond the neuropsychology of dreaming: Insights into the neural basis of dreaming with new techniques of sleep recording and analysis", Sleep Medicine Review 35, 2017.

* cited by examiner

SYSTEM AND METHOD TO ENHANCE DREAM RECALL

CROSS-REFERENCE TO PRIOR APPLICATIONS

This application claims the benefit of U.S. Provisional Application No. 62/945,906, filed on 10 Dec. 2019. This application is hereby incorporated by reference herein.

BACKGROUND

1. Field

The present disclosure pertains to a system and method for enhancing dream recall in a subject during a sleep session.

2. Description of the Related Art

Systems for monitoring sleep and delivering sensory stimulation to subjects during sleep are known. Electroencephalogram (EEG) sensor-based sleep monitoring and sensory stimulation systems are known.

SUMMARY

It would be advantageous to enhance dream recall following a sleep session. Delivery of repetitive sensory stimulation, at a particular frequency, to a subject during a sleep session may enhance dream recall following the sleep session. Accordingly, one or more aspects of the present disclosure relate to a system configured to deliver sensory stimulation to a subject during a sleep session in order to promote dream recall. The system comprises one or more sensors, one or more sensory stimulators, one or more processors, and/or other components. The one or more sensors are configured to generate output signals conveying information related to brain activity of the subject during the sleep session. The one or more sensory stimulators are configured to provide the sensory stimulation to the subject during the sleep session. The one or more processors are coupled to the one or more sensors and the one or more sensory stimulators. The one or more processors are configured by machine-readable instructions. The one or more processors are configured to control the one or more sensory stimulators based on the brain activity of the subject.

In some embodiments, the one or more sensors comprise one or more electroencephalogram (EEG) electrodes configured to generate the information related to brain activity. In some embodiments, the one or more processors are further configured to detect sleep in the subject. In some embodiments, the one or more processors may detect a sleep stage such as rapid eye movement (REM) sleep. In some embodiments, detecting sleep in the subject comprises causing a neural network to be trained based on the information related to the brain activity of the subject, as captured by the EEG electrodes. The trained neural network comprises an input layer, an output layer, and one or more intermediate layers between the input layer and the output layer. In some embodiments, an output of one or more intermediate layers of the neural network may be probabilities that a subject is in various sleep stages. In some embodiments, based on the output signals, the trained neural network may determine periods when the subject is experiencing REM sleep during the sleep session.

In some embodiments, once sleep (e.g., REM sleep) is detected, the one or more processors may control the one or more sensory stimulators to deliver sensory stimulation to the subject. In some embodiments, the sensory stimulation may be auditory, haptic, visual, and/or other stimulation. In some embodiments, the sensory stimulation may comprise repetitive stimulations having a constant inter-stimulation interval. In some embodiments, the interval may be approximately 160-200 milliseconds. In some embodiments, the frequency of the sensory stimulation may be in the theta range (e.g., 4-8 Hz). In some embodiments, the frequency of the sensory stimulation may be approximately in the theta range (e.g., not less than 2 Hz and not more than 10 Hz). In some embodiments, the system may monitor the output signals to determine the effect of the sensory stimulation on the brain activity of the subject. In some embodiments, the one or more processors may control the sensory stimulators to modulate the intensity of the sensory stimulation based on the output signals in order to enhance EEG theta power. In some embodiments, enhanced EEG theta power is associated with enhanced dream recall in the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
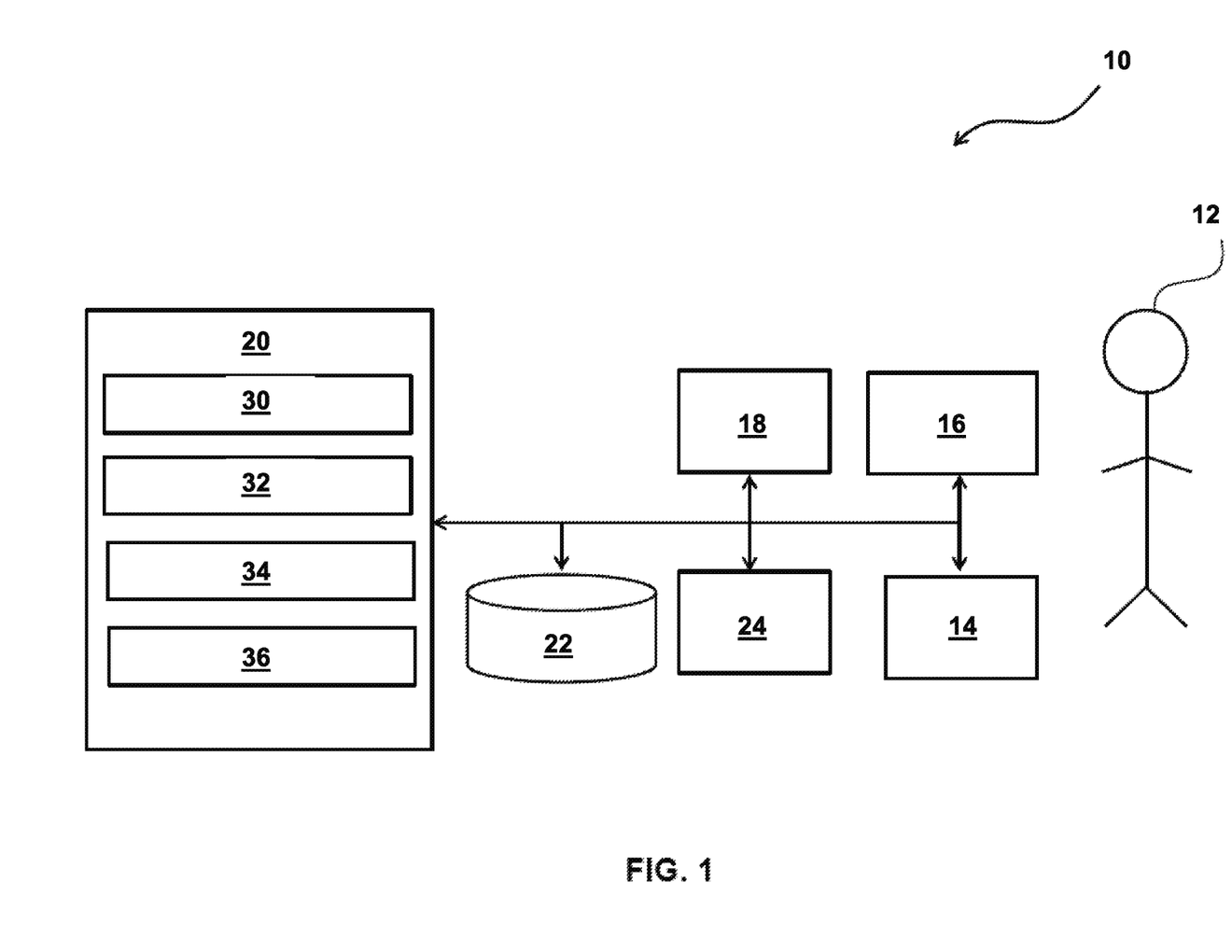
FIG. 1 is a schematic illustration of a system configured to enhance dream recall in a subject, in accordance with one or more embodiments.

FIG. 1 is a schematic illustration of a system 10 configured to enhance dream recall in a subject 12. System 10 is configured to facilitate delivery of sensory stimulation to subject 12 to enhance dream recall, adjust stimulation parameters based on the response of the subject to the sensory stimulation, and/or for other purposes. System 10 is configured such that sensory stimulation including auditory, haptic, visual, and/or other stimulation is delivered before and/or during sleep. In some embodiments, the initial intensity of the sensory stimulation (e.g., when entering a period of REM sleep) may be below a perceivable threshold. In some embodiments, the stimulation is modulated according to the brain activity of subject 12. In some embodiments, the brain activity is used to calculate an EEG theta power (e.g., running average of the square of the signal that results from filtering an EEG signal in the theta band) of the subject. In some embodiments, if the EEG theta power decreases during a time period, the one or more processors may control the sensory stimulators to increase the intensity of the sensory stimulation delivered to the subject. In some embodiments, the intensity of the sensory stimulation may be increased by a factor that is proportional to the EEG theta power decrease during the time period. In some embodiments, if the EEG theta power increases, the intensity of the sensory stimulation may remain the same. During the delivery of sensory stimulation, the brain activity of the subject may be monitored for micro-arousals such that the sensory stimulation does not wake the subject.

Delivering sensory stimulation to enhance the EEG theta power associated with the subject is important to dream recall. Higher frontal EEG theta power (e.g., 5-8 Hz) is associated with successful dream recall in subjects. Thus, by delivering sensory stimulation that increases EEG theta power in subjects during REM sleep, the system and method described herein may enhance dream recall following a sleep session. System 10 also leverages machine-learning models (e.g., deep neural networks and/or any other supervised machine learning algorithm as described below) for automatic, real-time or near real-time, closed loop, sensor output signals for determining the sleep stages of the subject during the sleep session. As shown in FIG. 1, system 10 includes one or more of a sensor 14, a sensory stimulator 16, external resources 18, a processor 20, electronic storage 22, a subject interface 24, and/or other components. These components are further described below.

Sensor 14 is configured to generate output signals conveying information related to sleep stages of subject 12 during a sleep session. The output signals conveying information related to sleep stages of subject 12 may include information related to brain activity in subject 12. As such, sensor 14 is configured to generate output signals conveying information related to brain activity. In some embodiments, sensor 14 is configured to generate output signals conveying information related to stimulation provided to subject 12 during sleep sessions (e.g., changes in brain activity of subject 12 resulting from the stimulation). In some embodiments, the information in the output signals from sensor 14 is used to control sensory stimulator 16 to provide sensory stimulation to subject 12 (as described below).

Sensor 14 may comprise one or more sensors that generate output signals that convey information related to brain activity in subject 12 directly. For example, sensor 14 may include electroencephalogram (EEG) electrodes configured to detect electrical activity along the scalp of subject 12 resulting from current flows within the brain of subject 12. Sensor 14 may comprise one or more sensors that generate output signals conveying information related to brain activity of subject 12 indirectly. For example, one or more sensors 14 may comprise a heart rate sensor that generates an output based on a heart rate of subject 12 (e.g., sensor 14 may be a heart rate sensor than can be located on the chest of subject 12, and/or be configured as a bracelet on a wrist of subject 12, and/or be located on another limb of subject 12), movement of subject 12 (e.g., sensor 14 may comprise an accelerometer that can be carried on a wearable, such as a bracelet around the wrist and/or ankle of subject 12 such that sleep may be analyzed using actigraphy signals), respiration of subject 12, and/or other characteristics of subject 12.

In some embodiments, sensor 14 may comprise one or more of EEG electrodes, a respiration sensor, a pressure sensor, a vital signs camera, a functional near infra-red sensor (fNIR), a temperature sensor, a microphone and/or other sensors configured to generate output signals related to (e.g., the quantity, frequency, intensity, and/or other characteristics of) the stimulation provided to subject 12, the brain activity of subject 12, and/or other sensors. Although sensor 14 is illustrated at a single location near subject 12, this is not intended to be limiting. Sensor 14 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), coupled with a bed and/or other furniture where subject 12 is sleeping, and/or in other locations.

Figure 2:
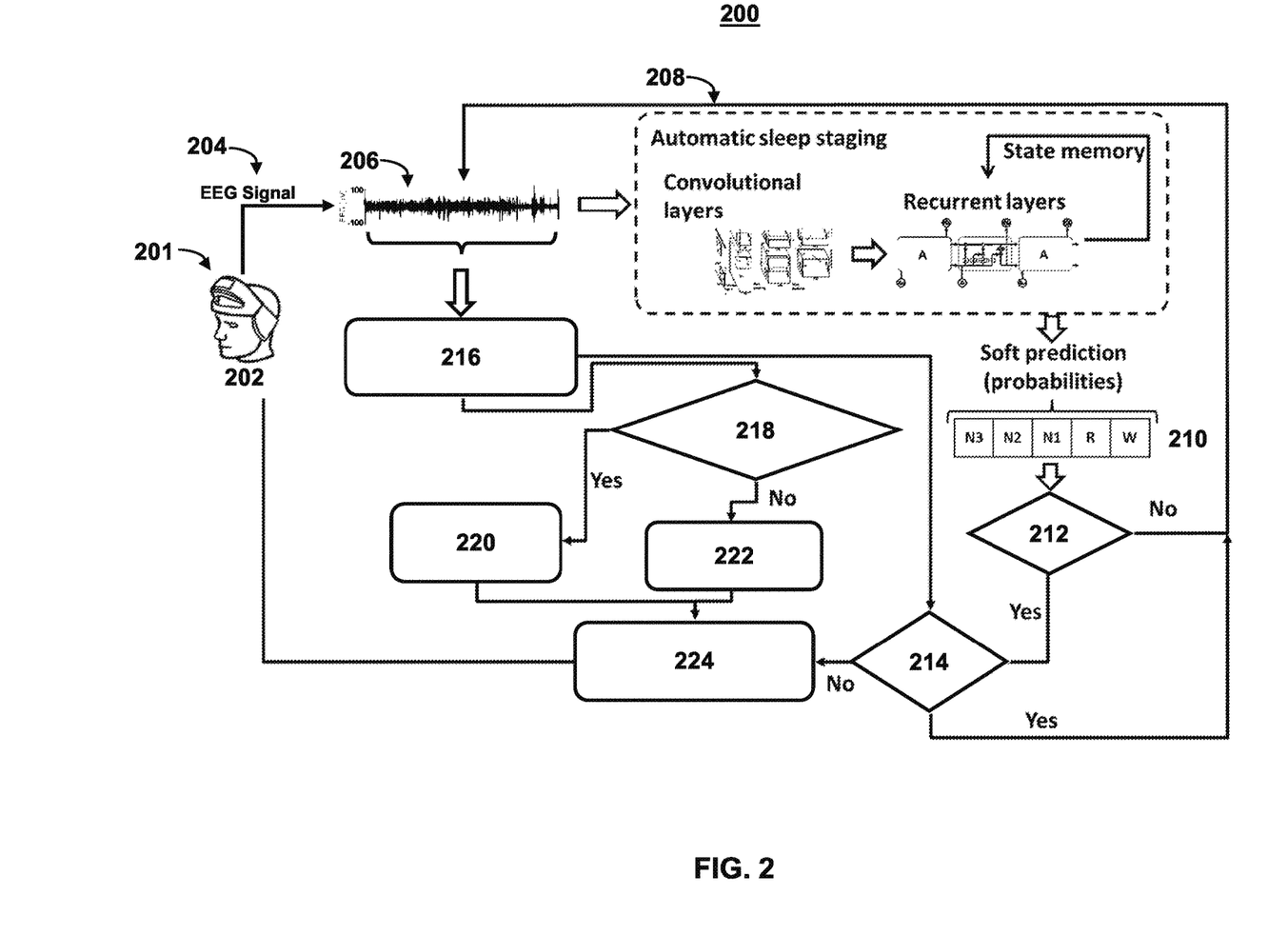
FIG. 2 illustrates several of the operations performed by the system, in accordance with one or more embodiments.

In FIG. 1, sensor 14, sensory stimulator 16, processor 20, electronic storage 22, and subject interface 24 are shown as separate entities. This is not intended to be limiting. Some and/or all of the components of system 10 and/or other components may be grouped into one or more singular devices. For example, these and/or other components may be included in a wearable device 201. In some embodiments, wearable device 201 may be a headset as illustrated in FIG. 2 and/or other garments worn by subject 12. Other garments may include a cap, vest, bracelet, and/or other garment. In some embodiments, wearable device 201 may comprise one or more sensors which may contact the skin of the subject. In some embodiments, wearable device 201 may comprise one or more sensory stimulators, which may provide auditory vibrations, haptic vibrations, light pulses, and/or other stimulation. For example, wearable device 201 and/or other garments may include, for example, sensing electrodes, a reference electrode, one or more devices associated with an EEG, means to deliver auditory stimulation (e.g., a wired and/or wireless audio device and/or other devices), and one or more audio speakers. In some embodiments, wearable device 201 may comprise means to delivery visual, somatosensory, electric, magnetic, and/or other stimulation to the subject. In this example, the audio speakers may be located in and/or near the ears of subject 12 and/or in other locations. The reference electrode may be located behind the ear of subject 12, and/or in other locations. In this example, the sensing electrodes may be configured to generate output signals conveying information related to brain activity of subject 12, and/or other information. The output signals may be transmitted to a processor (e.g., processor 20 shown in FIG. 1), a computing device (e.g., a bedside laptop) which may or may not include the processor, and/or other devices wirelessly and/or via wires. In this example, acoustic stimulation may be delivered to subject 12 via the wireless audio device and/or speakers. In this example, the sensing electrodes, the reference electrode, and the EEG devices may be represented, for example, by sensor 14 in FIG. 1. The wireless audio device and the speakers may be represented, for example, by sensory stimulator 16 shown in FIG. 1. In this example, a computing device may include processor 20, electronic storage 22, subject interface 24, and/or other components of system 10 shown in FIG. 1.

Sensory stimulator 16 is configured to provide sensory stimulation to subject 12. Sensory stimulator 16 is configured to provide auditory, visual, somatosensory, electric, magnetic, and/or sensory stimulation to subject 12 prior to a sleep session, during a sleep session, and/or at other times. In some embodiments, a sleep session may comprise any period of time when subject 12 is sleeping and/or attempting to sleep. Sleep sessions may include nights of sleep, naps, and/or other sleeps sessions. In some embodiments, the system may identify a sleep session through observation of the subject (e.g., via camera, light detection, etc.). For example, if the subject lies down, turns off the lights in a room that the subject is in, and/or lies still for certain amount of time, the system may identify that a sleep session has begun. In some embodiments, the system may identify that a sleep session has begun with the subject switches on a sleep device (e.g., a Philips SmartSleep device). For example, sensory stimulator 16 may be configured to provide stimuli to subject 12 during a sleep session to enhance EEG signals during sleep (e.g., REM sleep) in subject 12, and/or for other purposes.

Sensory stimulator 16 is configured to affect the EEG theta power associated with subject 12 through non-invasive brain stimulation and/or other methods. Sensory stimulator 16 may be configured to affect sleep through non-invasive brain stimulation using auditory, electric, magnetic, visual, somatosensory, and/or other sensory stimuli. The auditory, electric, magnetic, visual, somatosensory, and/or other sensory stimulation may include auditory stimulation, visual stimulation, somatosensory stimulation, electrical stimulation, magnetic stimulation, a combination of different types of stimulation, and/or other stimulation. The auditory, electric, magnetic, visual, somatosensory, and/or other sensory stimuli include odors, sounds, visual stimulation, touches, tastes, somatosensory stimulation, haptic, electrical, magnetic, and/or other stimuli. The sensory stimulation may have an intensity, a timing, and/or other characteristics. For example, stimulation may be provided to subject 12 to affect sleep in subject 12. The stimulation may comprise a continuous stimulation delivered to the subject. The acoustic tones may include one or more repeating stimulations of a determined length separated from each other by a constant inter-stimulation interval. The intensity (e.g., volume, strength, brightness, etc.) of the stimulation may be modulated based on various factors (as described herein). The pitch and tone may also be adjusted. In some embodiments, the intensity of the stimulation is modulated according to changes in the EEG theta power associated with the subject. For example, the initial intensity of the stimulation (e.g., at the beginning of a period of REM sleep) may be set below a perceivable threshold. If the one or more sensors detect a decrease in the EEG theta power associated with the subject over a time period (e.g., six seconds), the one or more processors may control the sensory stimulators to increase the intensity of the sensory stimulation in response to the detected decrease in the EEG theta power. In some embodiments, the intensity may be increased by a factor that is proportional to the decrease in the EEG theta power over the time period (e.g., six seconds). If the one or more sensors detect a lack of change in the EEG theta power associated with the subject over a time period, the one or more processors may control the sensory stimulators to increase the intensity of the sensory stimulation in response to the detected lack of change. In some embodiments, the intensity may be increased by a certain factor. If the one or more sensors detect an increase in the EEG theta power associated with the subject over a time period, the one or more processors may control the sensory stimulators to continue delivering the sensory stimulation to the subject at a constant intensity in response to the detected increase in EEG theta power. This example is not intended to be limiting, and stimulation modulation parameters may vary.

Examples of sensory stimulator 16 may include one or more of a sound generator, a speaker, a music player, a tone generator, a vibrator (such as a piezoelectric member, for example) to deliver vibratory stimulation, a coil generating a magnetic field to directly stimulate the brain's cortex, one or more light generators or lamps, a fragrance dispenser, and/or other devices. In some embodiments, sensory stimulator 16 is configured to adjust the intensity, timing, and/or other parameters of the stimulation provided to subject 12 (e.g., as described below).

External resources 18 include sources of information (e.g., databases, websites, etc.), external entities participating with system 10 (e.g., one or more the external sleep monitoring devices, a medical records system of a health care provider, etc.), and/or other resources. In some embodiments, external resources 18 include components that facilitate communication of information, one or more servers outside of system 10, a network (e.g., the internet), electronic storage, equipment related to Wi-Fi technology, equipment related to Bluetooth® technology, data entry devices, sensors, scanners, computing devices associated with individual subjects, and/or other resources. In some implementations, some or all of the functionality attributed herein to external resources 18 may be provided by resources included in system 10. External resources 18 may be configured to communicate with processor 20, subject interface 24, sensor 14, electronic storage 22, sensory stimulator 16, and/or other components of system 10 via wired and/or wireless connections, via a network (e.g., a local area network and/or the internet), via cellular technology, via Wi-Fi technology, and/or via other resources.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, subject interface 24, etc.), or processor 20 may represent processing functionality of a plurality of devices operating in coordination. In some embodiments, processor 20 may be and/or be included in a computing device such as a desktop computer, a laptop computer, a smartphone, a tablet computer, a server, and/or other computing devices. Such computing devices may run one or more electronic applications having graphical subject interfaces configured to facilitate subject interaction with system 10.

As shown in FIG. 1, processor 20 is configured to execute one or more computer program components. The computer program components may comprise software programs and/or algorithms coded and/or otherwise embedded in processor 20, for example. The one or more computer program components may comprise one or more of an information component 30, a model component 32, a control component 34, a modulation component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Information component 30 is configured to determine one or more brain activity parameters of subject 12, and/or other information. The brain activity parameters are determined based on the output signals from sensor 14 and/or other information. The brain activity parameters may indicate sleep in subject 12. In some embodiments, the information indicating sleep in the subject may be indicative of sleep stages of subject 12. For example, one of the sleep stages of subject 12 may be associated with rapid eye movement (REM) sleep, and/or other sleep. In some embodiments, the information in the output signals related to brain activity indicates a level of EEG theta power associated with the subject.

In some embodiments, the information related to brain activity that indicates EEG theta power is and/or includes EEG information and/or other information generated during sleep sessions of subject 12 and/or at other times. In some embodiments, brain activity parameters may be determined based on the EEG information and/or other information. In some embodiments, the brain activity parameters may be determined by information component 30 and/or other components of system 10. In some embodiments, the brain activity parameters may be previously determined and be part of the historical sleep stage information obtained from external resources 18 (described below). In some embodiments, the one or more brain activity parameters are and/or are related to a frequency, amplitude, phase, presence of specific sleep patterns such as eye movements, ponto-geniculo-occipital (PGO) wave, slow wave, and/or other characteristics of an EEG signal. In some embodiments, the one or more brain activity parameters are determined based on the frequency, amplitude, and/or other characteristics of the EEG signal. In some embodiments, the determined brain activity parameters and/or the characteristics of the EEG may be and/or indicate EEG theta power and/or sleep stages.

Information component 30 is configured to obtain historical sleep stage information. In some embodiments, the historical sleep stage information is for subject 12 and/or other subjects. The historical sleep stage information is related to brain activity, and/or other physiological of the population of subjects and/or subject 12 that indicates sleep stages over time during previous sleep sessions of subject 12 and/or other subjects. The historical sleep stage information is related to sleep stages and/or other brain parameters of subject 12 and/or other subjects during corresponding sleep sessions, and/or other information.

In some embodiments, information component 30 is configured to obtain the historical sleep stage information electronically from external resources 18, electronic storage 22, and/or other sources of information. In some embodiments, obtaining the historical sleep stage information electronically from external resources 18, electronic storage 22, and/or other sources of information comprises querying one or more databases and/or servers; uploading information and/or downloading information, facilitating subject input, sending and/or receiving emails, sending and/or receiving text messages, and/or sending and/or receiving other communications, and/or other obtaining operations. In some embodiments, information component 30 is configured to aggregate information from various sources (e.g., one or more of the external resources 18 described above, electronic storage 22, etc.), arrange the information in one or more electronic databases (e.g., electronic storage 22, and/or other electronic databases), normalize the information based on one or more features of the historical sleep stage information (e.g., length of sleep sessions, number of sleep sessions, etc.) and/or perform other operations.

Model component 32 is configured such that a trained neural network and/or any other supervised machine learning algorithms are caused to detect an EEG theta power and/or sleep in subject 12. In some embodiments, this may be and/or include determining periods when subject 12 is experiencing REM sleep during the sleep session and/or other operations. By way of a non-limiting example, a trained neural network may be caused to indicate determine the periods of REM sleep and/or timing of the REM sleep of the subject based on the output signals (e.g., using the information in the output signals as input for the model) and/or other information. In some embodiments, model component 32 is configured to provide the information in the output signals to the neural network in temporal sets that correspond to individual periods during the sleep session. In some embodiments, model component 32 is configured to cause the trained neural network to output the determined REM sleep of subject 12 during the sleep session based on the temporal sets of information. (The functionality of model component 32 is further discussed below relative to FIG. 2-3). In some embodiments, model component 32 is or includes the trained neural network.

Neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function that combines the values of all its inputs together. In some embodiments, each connection (or the neural unit itself) may have a threshold function such that a signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free flowing, with connections interacting in a more chaotic and complex fashion.

A trained neural network may comprise one or more intermediate or hidden layers. The intermediate layers of the trained neural network include one or more convolutional layers, one or more recurrent layers, and/or other layers of the trained neural network. Individual intermediate layers receive information from another layer as input and generate corresponding outputs. The detected sleep stages (e.g., REM sleep) are generated based on the information in the output signals from sensor 14 as processed by the layers of the neural network.

Control component 34 is configured to control stimulator 16 to provide stimulation to subject 12 during sleep and/or at other times. The stimulation may enhance dream recall (e.g., as described herein) and/or have other purposes. Control component 34 is configured to cause sensory stimulator 16 to provide modulated sensory stimulation to subject 12 during a sleep session. In some embodiments, control component 34 is configured to cause sensory stimulator 16 to modulate the sensory stimulation delivered to subject 12 based on a change in EEG theta power associated with subject 12 (e.g., the output from model component 32) and/or other information. In some embodiments, control component 34 is configured to cause sensory stimulator 16 to modulate the sensory stimulation to subject 12 based on a detected change in EEG theta power and/or other information over time during the sleep session. Control component 34 is configured to cause sensory stimulator 16 to increase the intensity of sensory stimulation to subject 12 responsive to a decrease or a lack of change in the EEG theta power associated with subject 12. For example, control component 34 is configured such that controlling one or more sensory stimulators 16 to modulate the sensory stimulation to subject 12 during the sleep session comprises: detecting sleep (e.g., REM sleep) in the subject during a sleep session, and controlling the one or more sensory stimulators to delivery sensory stimulation to the subject during the sleep session. In some embodiments, the one or more processors may control the one or more sensory stimulators to increase the intensity of the sensory stimulation in response to a lack of change or a decrease in the EEG theta power associated with the subject over a time period (as described herein).

In some embodiments, control component 34 is configured to control sensory stimulator 16 to modulate an intensity of the sensory stimulation delivered to subject 12 responsive to model component 32 determining that the subject is in REM sleep and that the EEG theta power associated with the subject 12 has decreased or remained the same during a time period (e.g., six seconds). For example, model component 32 and/or control component 34 may be configured such that on detection of REM sleep, model component 32 starts a (physical or virtual) timer configured to track the time subject 12 spends in REM sleep. Control component 34 is configured to control stimulation responsive to the duration that subject 12 spends in continuous REM sleep breaching a predefined duration threshold. In some embodiments, the predefined duration threshold is determined at manufacture of system 10 and/or at other times. In some embodiments, the predefined duration threshold is determined based on information from previous sleep sessions of subject 12 and/or subjects demographically similar to subject 12 (e.g., as described above). In some embodiments, the predefined duration threshold is adjustable via subject interface 24 and/or other adjustment mechanisms.

Modulation component 36 is configured to cause sensory stimulator 16 to modulate an amount, a timing, and/or intensity of the sensory stimulation. Modulation component 36 is configured to cause sensory stimulator 16 to modulate the amount, timing, and/or intensity of the sensory stimulation based on the brain activity parameters, values output from the intermediate layers of the trained neural network, and/or other information. As an example, sensory stimulator 16 is caused to modulate the timing and/or intensity of the sensory stimulation based on the brain activity parameters, the values output from the convolutional layers, the values output from the recurrent layers, and/or other information. For example, modulation component 36 may be configured such that sensory stimulation is delivered with an intensity that varies according to changes in EEG theta power associated with subject 12. In this example, decreases or lack of changes in the EEG theta power cause the modulation component 36 to increase the intensity of the stimulation delivered to subject 12. If sleep micro-arousals are detected, modulation component 36 may be configured such that the sensory stimulation ceases.

By way of a non-limiting example, FIG. 2 illustrates several of the operations performed by system 10 (FIG. 1) and described above. In the example shown in process 200 of FIG. 2, an EEG signal 204 of subject 202 (e.g., similar to and/or the same as subject 12 shown in FIG. 1) is processed (e.g., by information component 30 and model component 32 shown in FIG. 1) in temporal window 206. In some embodiments, temporal window 206 may comprise six-second increments of EEG signal 204. In some embodiments, EEG signal 204 may be processed by a deep neural network. A deep neural network may determine sleep depth and stage information of the subject (as described below in relation to FIG. 3). In some embodiments, methods described in the publication "Recurrent Deep Neural Networks for Real-Time Sleep Stage Classification From Single Channel EEG." *Frontiers in Computational Neuroscience*. Bresch, E., Großekathöfer, U., and Garcia-Molina, G. (2018), which is hereby incorporated by reference in its entirety, may be utilized.

As shown in FIG. 2, process 200 may determine sleep stage probabilities using deep learning algorithm 208 (e.g., as described below in relation to deep neural network architecture 300 of FIG. 3). In some embodiments, deep learning algorithm 208 outputs soft prediction probabilities 210. Soft prediction probabilities 210 are prediction probabilities for individual sleep stages. The set of soft prediction probabilities 210 constitute a so-called soft decision vector, which may be translated into a hard decision by determining which sleep stage is associated with a highest probability value (in a continuum of possible values) relative to other sleep stages. These soft decisions make it possible for system 10 (FIG. 1) to consider different possible sleep states on a continuum rather than being forced to decide which discrete sleep stage "bucket" particular EEG information fits into (as in prior art systems). The terms "soft" and "hard" are not intended to be limiting but may be helpful to use to describe the operations performed by the system. For example, the term "soft output" may be used, because at this stage, any decision is possible. Indeed, the final decision could depend on post-processing of the soft outputs, for example.

Process 200 may then determine if subject 12 (FIG. 1)/202 is in REM sleep 212. In some embodiments, system 10 may determine if subject 12/202 is in REM sleep based on soft prediction probabilities 210. In some embodiments, if a sleep stage other than REM sleep has the highest probability, system 10 may determine that subject 12/202 is not in REM sleep. If the subject is not in REM sleep 212, process 200 returns to temporal window 206 and continues to predict the sleep stages (e.g., soft prediction probabilities 210) until it is determined that subject 12/202 is in REM sleep 212. In some embodiments, if the sleep stage with the highest probability is REM sleep, then system 10 may determine that subject 12/202 is in REM sleep. If the subject is in REM sleep 212, process 200 determines if there are micro-arousals 214. Micro-arousals 214 are identified using thresholds for instantaneous alpha and instantaneous beta power values (i.e., of the EEG signal). In some embodiments, the alpha band of the EEG signal has a frequency between 8-12 Hz. In some embodiments, the beta band of the EEG signal has a frequency between 15-30 Hz. If the instantaneous EEG alpha power breaches a first arousal threshold (e.g., 13 microvolts (RMS units)) for a predetermined period of time (e.g., at least 500-millisecond) or the instantaneous EEG beta power breaches a second arousal threshold (e.g., 2 microvolts (RMS units)) for a predetermined period of time (e.g., at least 500-millisecond), then a sleep micro-arousal is detected.

If a micro-arousal 214 is detected, process 200 returns to temporal window 206 and continues to predict the sleep stages (e.g., soft prediction probabilities 210) until it is determined that subject 12 (FIG. 1)/202 is once again in REM sleep 212. If no micro-arousals are detected, process 200 delivers sensory stimulation 224 to subject 12/202 to increase the EEG theta power (to enhance dream recall). In some embodiments, the sensory stimulation may be auditory, haptic, visual, or other stimulation. In some embodiments, the sensory stimulation may have a frequency in the theta range (e.g., 4-8 Hz). The stimulation may comprise a continuous stimulation delivered to the subject. The acoustic tones may include one or more series of repeating stimulations of a determined length separated from each other by a constant inter-stimulation interval. The intensity (e.g., the volume) of the stimulation may be modulated according to changes in the EEG theta power the subject (as described herein).

Process 200 continues to monitor temporal window 206 during delivery of sensory stimulation 224 to subject 12. System 10 may calculate EEG theta, beta, and alpha powers 216 based on the EEG signal 204 in temporal window 206. System 10 (FIG. 1) may compare the alpha and beta powers of the EEG signal 204 to pre-defined arousal thresholds (as described above) in order to detect micro-arousals 214. If a micro-arousal 214 is detected, process 200 ceases delivering sensory stimulation 224 to subject 202 and process 200 returns to monitoring temporal window 206 for REM sleep 212. In some embodiments, system 10 may utilize the EEG theta power to modulate the intensity of the sensory stimulation delivered to subject 12/202. For example, the initial intensity of the stimulation (e.g., at the beginning of a period of REM sleep) may be set below a perceivable threshold. The one or more sensors of system 10 may determine whether the EEG theta power 218 increased over a time period (e.g., six seconds or another time period). In response to a detected lack of change or a detected decrease in the EEG theta power 218 over the time period, the sensory stimulators may change the stimulation settings 222 to increase the intensity of the sensory stimulation. If the one or more sensors detect a decrease in the EEG theta power associated with the subject over a time period (e.g., six seconds), the one or more processors may control the sensory stimulators to increase the intensity of the sensory stimulation. In some embodiments, the intensity may be increased by a factor that is proportional to the decrease in the EEG theta power over the time period. In some embodiments, the intensity may be increased by another factor. If the one or more sensors detect a lack of change in the EEG theta power associated with the subject over a time period, the one or more processors may control the sensory stimulators to increase the intensity of the sensory stimulation. In some embodiments, the intensity may be increased by a certain factor. In some embodiments, if the one or more sensors of system 10 detect an increase in the EEG theta power 218 over the time period, the sensory stimulators may continue delivering the sensory stimulation to the subject at a constant intensity 220.

Figure 3:
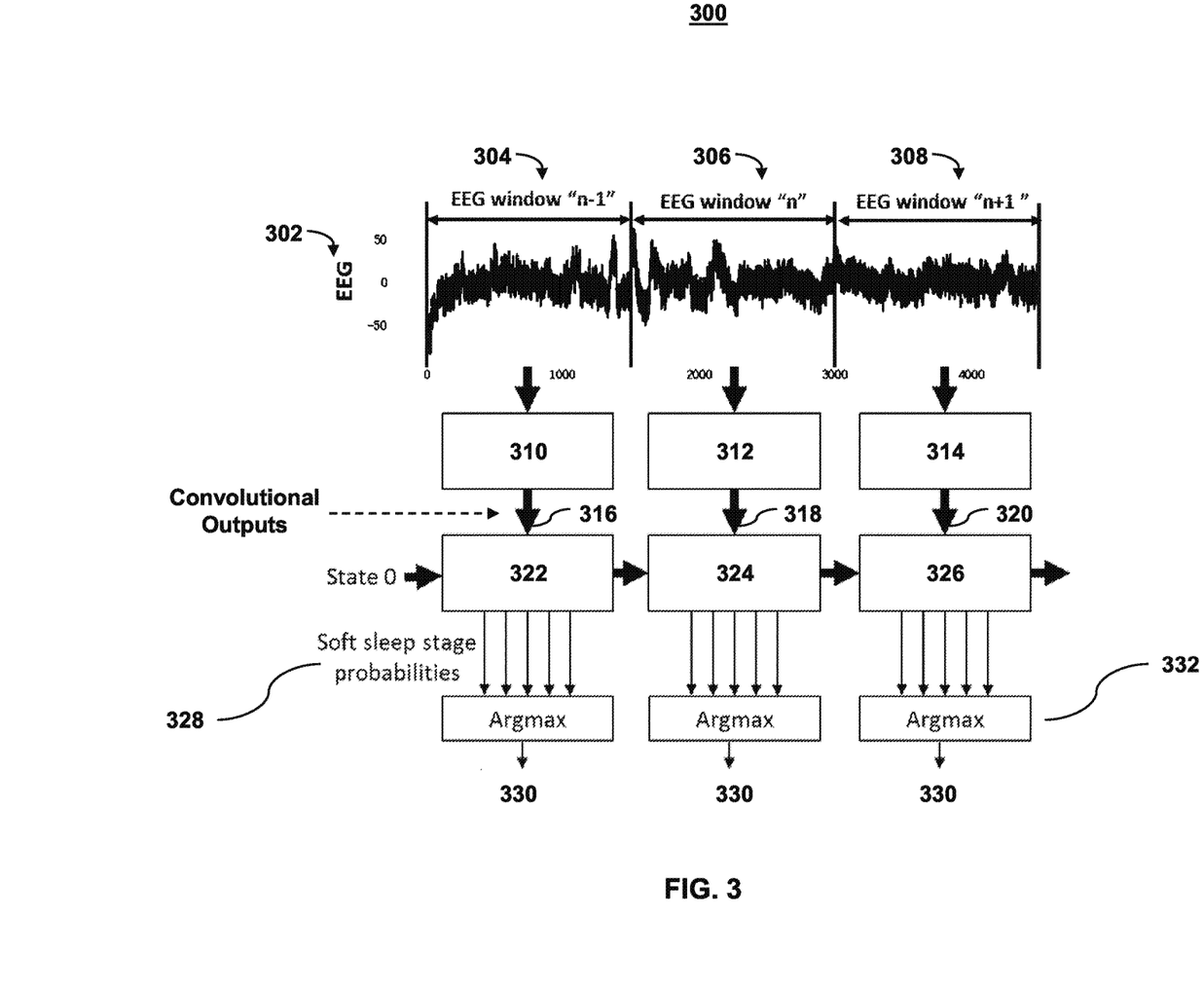
FIG. 3 illustrates example architecture of a deep neural network that is part of the system, in accordance with one or more embodiments.

FIG. 3 illustrates example architecture 300 of a deep neural network (e.g., for processing temporal window 206, as shown in FIG. 2) that is part of system 10 (FIGS. 1 and 2). FIG. 3 illustrates deep neural network architecture 300 for three (unrolled) EEG windows 304, 306, and 308. In some embodiments, windows 304, 306, and 308 may be windows of an EEG signal 302 for pre-defined time periods (e.g., six seconds). Architecture 300 includes convolutional layers 310, 312, and 314, and recurrent layers 322, 324, and 326. As described above, convolutional layers 310, 312, and 314 can be thought of as filters and produce convolution outputs 316, 318, and 320 that are fed to recurrent layers 322, 324, and 326 (LSTM (long short term memory) layers in this example). The output of architecture 300 for individual windows 304, 306, and 308 that are processed are a set of prediction probabilities for individual sleep stages, which are termed "soft output(s)" 328. "Hard" predictions 330 are determined by architecture 300 (model component 32 shown in FIG. 1) by predicting 332 a sleep stage associated with a "soft" output with the highest value (e.g., as described below). The terms "soft" and "hard" are not intended to be limiting but may be helpful to use to describe the operations performed by the system. For example, the term "soft output" may be used, because at this stage, any decision is possible. Indeed, the final decision could depend on post-processing of the soft outputs, for example. "Argmax" in FIG. 3 is an operator that indicates the sleep stage associated with the highest "soft output" (e.g., the highest probability).

For example, a useful property of neural networks is that they can produce probabilities associated with pre-defined sleep stages (e.g., Wake, REM, N1, N2, N3 sleep). Model component 32 (FIG. 1) is configured such that the set of probabilities constitute a so-called soft decision vector, which may be translated into a hard decision by determining which sleep stage is associated with a highest probability value (in a continuum of possible values) relative to other sleep stages. These soft decisions make it possible for system 10 to consider different possible sleep states on a continuum rather than being forced to decide which discrete sleep stage "bucket" particular EEG information fits into (as in prior art systems). In some embodiments, other methods of determining sleep stages may be used to determine the sleep stage of the subject (e.g., 12, as shown in FIG. 1) in addition to or instead of the systems described herein. For example, systems using two or more EEG signals may be used to determine the sleep stage of the subject.

Returning to FIG. 1, model component 32 is configured such that both the values output from convolutional layers, and the soft decision value outputs, are vectors comprising continuous values as opposed to discrete values such as sleep stages. Consequently, convolutional and recurrent (soft decision) value outputs are available to be used by system 10 to modulate the intensity of the stimulation according to changes in EEG theta power associated with the subject during sleep (e.g., a period of uninterrupted REM sleep). As described herein, modulation parameters may be determined (e.g., using information component 30 shown in FIG. 1) based on the raw sensor output signals (e.g., EEG signals).

As described above, modulation component 36 is configured to cause sensory stimulator 16 to modulate an amount, timing, and/or intensity of the sensory stimulation. This may be done to enhance dream recall, and/or for other purposes. Modulation component 36 is configured to cause sensory stimulator to modulate the amount, timing, and/or intensity of the sensory stimulation based on the one or more brain activity and/or other parameters, values output from the convolutional and/or recurrent layers of the trained neural network, and/or other information. As an example, volume of auditory vibration, the strength of haptic vibration, the brightness of visual stimulation, and/or intensity of another type of stimulation intensities may be adjusted and/or otherwise controlled (e.g., modulated) based on value outputs from the deep neural network such as convolutional layer value outputs and recurrent layer value outputs (e.g., sleep stage (soft) prediction probabilities). In some embodiments, modulation component 36 is configured to cause one or more sensory stimulators 16 to cease delivery of sensory stimulation and/or decrease the intensity of the sensory stimulation responsive to an indication that subject 12 is experiencing one or more micro-arousals.

In some embodiments, modulation component 36 is configured to modulate the sensory stimulation based on the brain activity and/or other parameters alone, which may be determined based on the output signals from sensors 14 (e.g., based on a raw EEG signal). In these embodiments, the output of a deep neural network (and/or other machine learning models) continues to be used to detect sleep stages (e.g., REM sleep), as described above. However, the stimulation intensity may instead be modulated based on brain activity and/or other parameters or properties determined based on the sensor output signals (e.g., EEG theta power and/or other parameters). In some embodiments, the information in, or determined based on, the sensor output signals can also be combined with intermediate outputs of the network such as output of the convolution layers or the final outputs (soft stages) to modulate intensity (e.g., as described herein).

Figure 4:
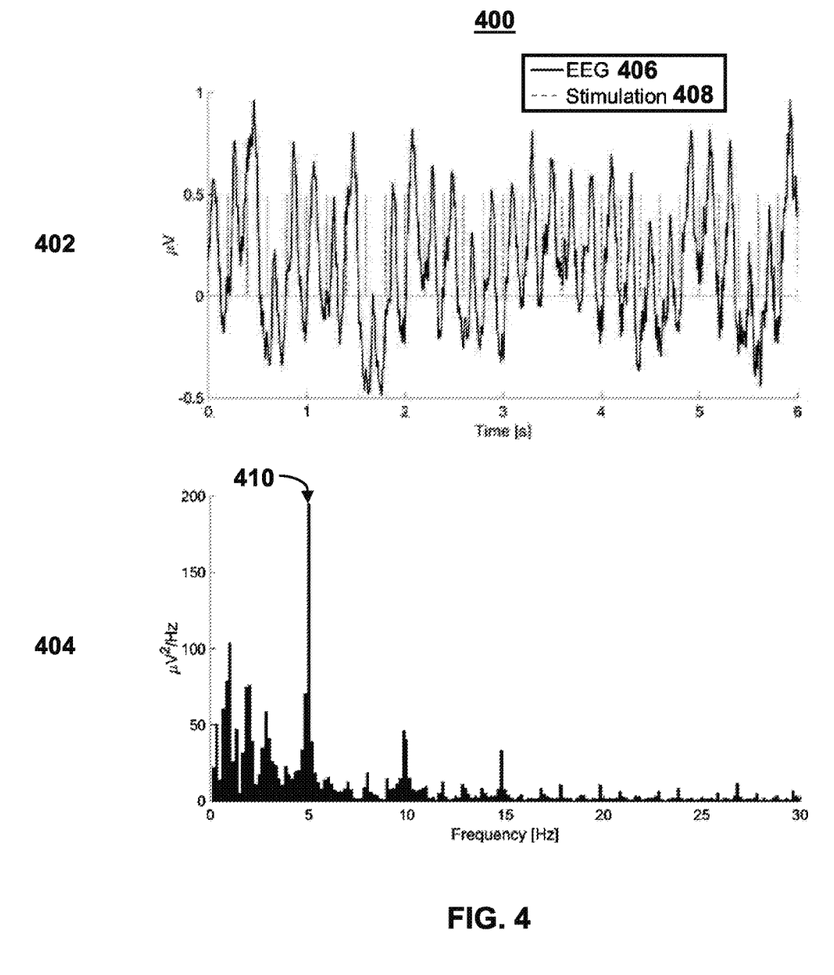
FIG. 4 illustrates brain activity of a subject during delivery of sensory stimulation, in accordance with one or more embodiments.

FIG. 4 illustrates brain activity 400 of a subject during delivery of sensory stimulation to a subject (e.g., 12, as shown in FIG. 1, and/or 202, as shown in FIG. 2) during a sleep session. As illustrated by brain activity 400, graph 402 shows timing of the stimulation 408 delivered to subject 12 and the EEG signal 406 of subject 12. As shown in graph 402, the timing of the waves of the EEG signal 406 align with the frequency of stimulation 408 (e.g., 5 Hz). For example, after two seconds of stimulation 408, EEG signal 406 has a frequency of approximately 5 Hz (i.e., matching the frequency of stimulation 408). This is shown in spectrogram 404, which shows a peak 410 at 5 Hz. Brain activity 400 thus illustrates delivery of sensory stimulation to a subject (e.g., 12, as shown in FIG. 1, and/or 202, as shown in FIG. 2) in order to increase EEG theta power, in accordance with process 200 (e.g., as shown in FIG. 2).

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 22 may store software algorithms, information determined by processor 20, information received via subject interface 24 and/or external computing systems (e.g., external resources 18), and/or other information that enables system 10 to function as described herein. Electronic storage 22 may be (in whole or in part) a separate component within system 10, or electronic storage 22 may be provided (in whole or in part) integrally with one or more other components of system 10 (e.g., processor 20).

Subject interface 24 is configured to provide an interface between system 10 and subject 12, and/or other subjects through which subject 12 and/or other subjects may provide information to and receive information from system 10. This enables data, cues, results, and/or instructions and any other communicable items, collectively referred to as "information," to be communicated between a subject (e.g., subject 12) and one or more of sensor 14, sensory stimulator 16, external resources 18, processor 20, and/or other components of system 10. For example, a hypnogram, EEG data, REM sleep stage probability, and/or other information may be displayed for subject 12 or other subjects via subject interface 24. As another example, subject interface 24 may be and/or be included in a computing device such as a desktop computer, a laptop computer, a smartphone, a tablet computer, and/or other computing devices. Such computing devices may run one or more electronic applications having graphical subject interfaces configured to provide information to and/or receive information from subjects.

Examples of interface devices suitable for inclusion in subject interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, subject interface 24 comprises a plurality of separate interfaces. In some embodiments, subject interface 24 comprises at least one interface that is provided integrally with processor 20 and/or other components of system 10. In some embodiments, subject interface 24 is configured to communicate wirelessly with processor 20 and/or other components of system 10.

It is to be understood that other communication techniques, either hard-wired or wireless, are also contemplated by the present disclosure as subject interface 24. For example, the present disclosure contemplates that subject interface 24 may be integrated with a removable storage interface provided by electronic storage 22. In this example, information may be loaded into system 10 from removable storage (e.g., a smart card, a flash drive, a removable disk, etc.) that enables the subject(s) to customize the implementation of system 10. Other exemplary input devices and techniques adapted for use with system 10 as subject interface 24 comprise, but are not limited to, an RS-232 port, RF link, an IR link, modem (telephone, cable or other). In short, any technique for communicating information with system 10 is contemplated by the present disclosure as subject interface 24.

Figure 5:
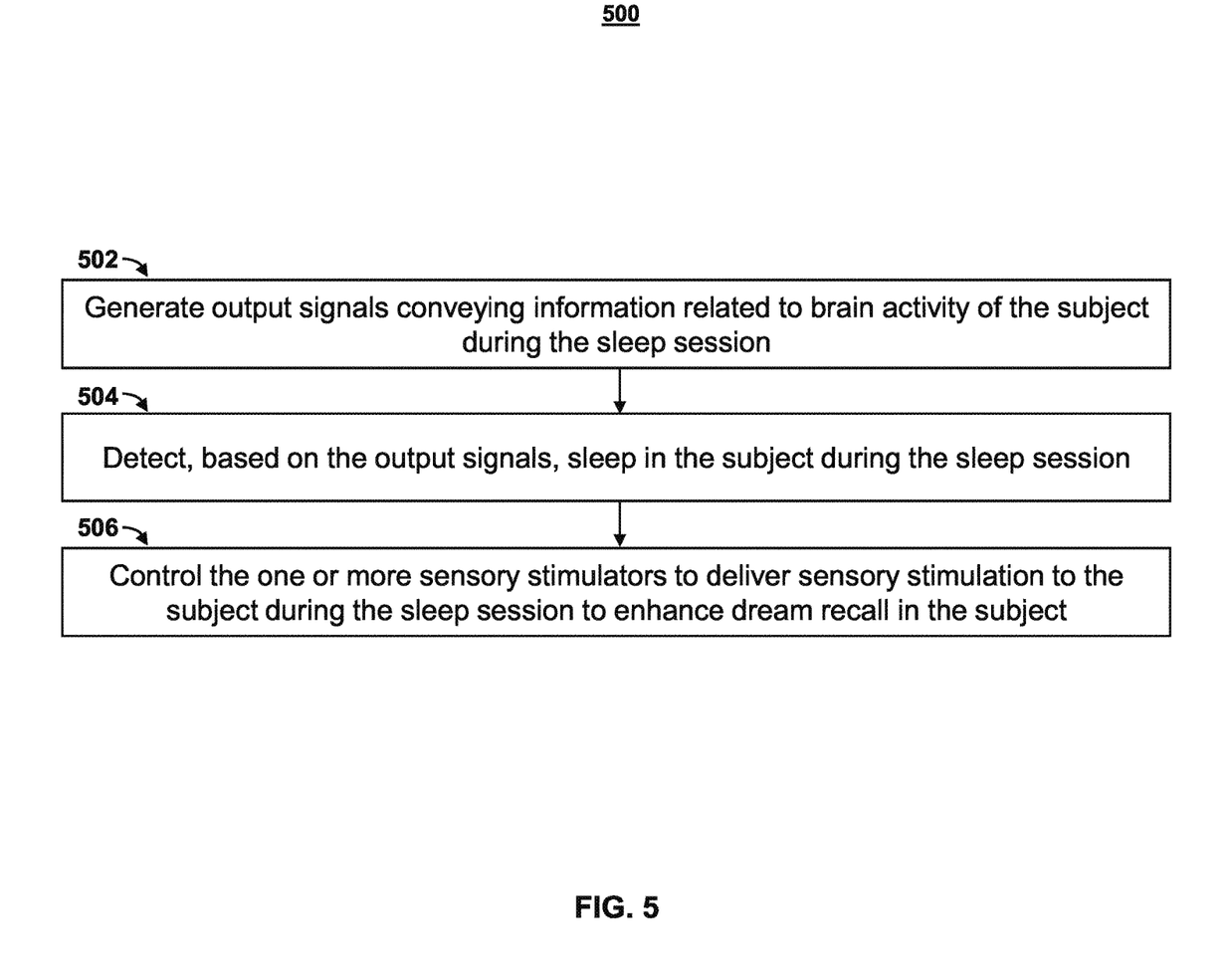
FIG. 5 illustrates a method for enhancing dream recall in a subject, in accordance with one or more embodiments.

FIG. 5 illustrates method 500 for enhancing dream recall in a subject (e.g., 12, as shown in FIG. 1, and/or 202, as shown in FIG. 2). The system comprises one or more sensors, one or more sensory stimulators, one or more processors configured by machine-readable instructions, and/or other components. The one or more processors are configured to execute computer program components. The computer program components comprise an information component, a model component, a control component, a modulation component, and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices such as one or more processors 20 described herein (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, output signals conveying information related to brain activity of the subject during the sleep session are generated. The output signals are generated during a sleep session of the subject and/or at other times. In some embodiments, operation 502 is performed by sensors the same as or similar to sensors 14 (shown in FIG. 1 and described herein).

In some embodiments, operation 502 includes providing the information in the output signals to the neural network in temporal sets that correspond to periods of time during the sleep session. In some embodiments, operation 504 includes causing the trained neural network to output detected REM sleep for the subject during the sleep session based on the temporal sets of information. In some embodiments, operation 502 is performed by a processor component the same as or similar to model component 32 (shown in FIG. 1 and described herein).

At an operation 504, sleep is detected in the subject (e.g., 12, as shown in FIG. 1) during the sleep session. In some embodiments, sleep is detected by determining sleep stage probabilities using a deep neural network (e.g., as described in relation to FIG. 3). In some embodiments, it is determined that the subject is asleep when the highest probability output by a deep neural network is a sleep stage (e.g., REM, N1, N2, N3 sleep, etc.). In some embodiments, the system may identify REM sleep in the subject (e.g., as the highest probability output of the deep neural network described in FIG. 3). In some embodiments, operation 504 is performed by a processor component the same as or similar to control component 34 (shown in FIG. 1 and described herein).

At an operation 506, the one or more sensory stimulators are controlled to deliver sensory stimulation to the subject during the sleep session to enhance dream recall in the subject. For example, upon detection of sleep (e.g., REM sleep) in the subject, the one or more processors may control the one or more sensory stimulators to deliver sensory stimulation (e.g., auditory, haptic, visual, and/or other stimulation) to the subject (e.g., 12, as shown in FIG. 1, and/or 202, as shown in FIG. 2). In some embodiments, the intensity (e.g., volume, strength, brightness, etc.) of the sensory stimulation may be modulated based on one or more brain activity parameters of the subject (e.g., instantaneous EEG theta power, as described in relation to FIG. 2). For example, a decrease or lack of change in EEG theta power may cause the one or more processors to control the one or more sensory stimulators to increase the intensity of the sensory stimulation. An increase in EEG theta power may cause the one or more processors to control the one or more sensory stimulators to continue delivering the sensory stimulation at a constant intensity. In some embodiments, operation 506 is performed by a processor component the same as or similar to control component 34 and/or modulation component 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for enhancing dream recall in a subject, the system comprising:
one or more sensors configured to generate output signals conveying information related to brain activity of a subject during a sleep session;
one or more sensory stimulators configured to provide sensory stimulation to the subject; and
one or more processors operatively coupled to the one or more sensors and the one or more sensory stimulators, the one or more processors configured by machine-readable instructions to:
detect, based on the output signals, rapid eye movement (REM) sleep in the subject during the sleep session;

control the one or more sensory stimulators to deliver the sensory stimulation to the subject during the REM sleep to enhance the dream recall in the subject;
determine, based on the output signals, an electroencephalogram (EEG) for the subject during the sleep session;
determine a theta power for the EEG; and
control the one or more sensory stimulators to deliver the sensory stimulation to the subject during the REM sleep to enhance the EEG theta power, the enhanced EEG theta power being associated with the dream recall in the subject, wherein, to control the one or more sensory stimulators to deliver the sensory stimulation to the subject during the REM sleep to enhance the EEG theta power, the one or more processors are further configured to:
detect, based on the output signals, an increase in the EEG theta power associated with the subject during the REM sleep; and
cause the one or more sensory stimulators to deliver the sensory stimulation to the subject at a constant intensity based on the detected increase in the EEG theta power.

2. The system of claim 1, wherein the sensory stimulation delivered to the subject comprises repeating stimulations each separated from one another by a constant interval.

3. The system of claim 1, wherein the one or more processors are further configured to: calculate, based on the output signals, an instantaneous EEG alpha power;
compare the instantaneous EEG alpha power to a first arousal threshold;
in response to determining that the instantaneous EEG alpha power breaches the first arousal threshold for a predetermined period of time, cause the one or more sensory stimulators to cease delivering the sensory stimulation to the subject.

4. The system of claim 1, wherein the one or more processors are further configured to: calculate, based on the output signals, an instantaneous EEG beta power;
compare the instantaneous EEG beta power to a second arousal threshold; and
in response to determining that the instantaneous EEG beta power breaches the second arousal threshold for a predetermined period of time, cause the one or more sensory stimulators to cease delivering the sensory stimulation to the subject.

5. A system for enhancing dream recall in a subject, the system comprising:
one or more sensors configured to generate output signals conveying information related to brain activity of a subject during a sleep session;
one or more sensory stimulators configured to provide sensory stimulation to the subject; and
one or more processors operatively coupled to the one or more sensors and the one or more sensory stimulators, the one or more processors configured by machine-readable instructions to:
detect, based on the output signals, rapid eye movement (REM) sleep in the subject during the sleep session;
control the one or more sensory stimulators to deliver the sensory stimulation to the subject during the REM sleep to enhance the dream recall in the subject;
determine, based on the output signals, an electroencephalogram (EEG) for the subject during the sleep session;
determine a theta power for the EEG; and
control the one or more sensory stimulators to deliver the sensory stimulation to the subject during the REM sleep to enhance the EEG theta power, the enhanced EEG theta power being associated with the dream recall in the subject, wherein, to control the one or more sensory stimulators to deliver the sensory stimulation to the subject during the REM sleep to enhance the EEG theta power, the one or more processors are further configured to:
detect, based on the output signals, a lack of change in the EEG theta power associated with the subject during the REM sleep; and
cause the one or more sensory stimulators to increase an intensity of the sensory stimulation delivered to the subject based on the detected lack of change in the EEG theta power.

6. A system for enhancing dream recall in a subject, the system comprising:
one or more sensors configured to generate output signals conveying information related to brain activity of a subject during a sleep session;
one or more sensory stimulators configured to provide sensory stimulation to the subject; and
one or more processors operatively coupled to the one or more sensors and the one or more sensory stimulators the one or more processors configured by machine-readable instructions to:
detect, based on the output signals, rapid eye movement (REM) sleep in the subject during the sleep session;
control the one or more sensory stimulators to deliver the sensory stimulation to the subject during the REM sleep to enhance the dream recall in the subject;
determine, based on the output signals, an electroencephalogram (EEG) for the subject during the sleep session;
determine a theta power for the EEG; and
control the one or more sensory stimulators to deliver the sensory stimulation to the subject during the REM sleep to enhance the EEG theta power, the enhanced EEG theta power being associated with the dream recall in the subject, wherein, to control the one or more sensory stimulators to deliver the sensory stimulation to the subject during the REM sleep to enhance the EEG theta power, the one or more processors are further configured to:
detect, based on the output signals, a decrease in the EEG theta power associated with the subject during the REM sleep; and
cause the one or more sensory stimulators to increase an intensity of the sensory stimulation delivered to the subject based on the detected decrease in the EEG theta power.

7. The system of claim 6, wherein the intensity of the sensory stimulation delivered to the subject is increased by a factor proportional to the decrease in the EEG theta power.

8. A method for enhancing dream recall in a subject with a system, the system comprising one or more sensors, one or more sensory stimulators, and one or more processors, the method comprising:
generating, with the one or more sensors, output signals conveying information related to brain activity of the subject during a sleep session;
detecting based on the output signals rapid eye movement (REM) sleep in the subject during the sleep session;

controlling the one or more sensory stimulators to deliver the sensory stimulation to the subject during the REM sleep to enhance the dream recall in the subject;

determining, based on the output signals, an electroencephalogram (EEG) for the subject during the sleep session;

determining a theta power for the EEG; and controlling the one or more sensory stimulators to deliver the sensory stimulation to the subject during the REM sleep to enhance the EEG theta power, the enhanced EEG theta power being associated with the dream recall in the subject wherein controlling the one or more sensory stimulators to deliver the sensory stimulation to the subject during the REM sleep to enhance the EEG theta power comprises:

detecting, based on the output signals, an increase in the EEG theta power associated with the subject during the REM sleep; and causing the one or more sensory stimulators to deliver the sensory stimulation to the subject at a constant intensity based on the detected increase in the EEG theta power.

9. The method of claim 8, wherein the sensory stimulation delivered to the subject comprises repeating stimulations each separated from one another by a constant interval.

10. The method of claim 8, further comprising:

calculating, based on the output signals, an instantaneous EEG alpha power;

comparing the instantaneous EEG alpha power to a first arousal threshold;

in response to determining that the instantaneous EEG alpha power breaches the first arousal threshold for a predetermined period of time, causing the one or more sensory stimulators to cease delivering the sensory stimulation to the subject.

11. The method of claim 8, further comprising:

calculating, based on the output signals, an instantaneous EEG beta power;

comparing the instantaneous EEG beta power to a second arousal threshold; and in response to determining that the instantaneous EEG beta power breaches the second arousal threshold for a predetermined period of time, causing the one or more sensory stimulators to cease delivering the sensory stimulation to the subject.

12. A method for enhancing dream recall in a subject with a system, the system comprising one or more sensors, one or more sensory stimulators, and one or more processors, the method comprising:

generating, with the one or more sensors, output signals conveying information related to brain activity of the subject during a sleep session;

detecting, based on the output signals, rapid eye movement (REM) sleep in the subject during the sleep session;

controlling the one or more sensory stimulators to deliver the sensory stimulation to the subject during the REM sleep to enhance the dream recall in the subject;

determining, based on the output signals, an electroencephalogram (EEG) for the subject during the sleep session;

determining a theta power for the EEG; and controlling the one or more sensory stimulators to deliver the sensory stimulation to the subject during the REM sleep to enhance the EEG theta power, the enhanced EEG theta power being associated with the dream recall in the subject, wherein controlling the one or more sensory stimulators to deliver the sensory stimulation to the subject during the REM sleep to enhance the EEG theta power comprises:

detecting, based on the output signals, a lack of change in the EEG theta power associated with the subject during the REM sleep; and causing the one or more sensory stimulators to increase an intensity of the sensory stimulation delivered to the subject based on the detected lack of change in the EEG theta power.

13. A method for enhancing dream recall in a subject with a system, the system comprising one or more sensors, one or more sensory stimulators, and one or more processors, the method comprising:

generating, with the one or more sensors, output signals conveying information related to brain activity of the subject during a sleep session;

detecting, based on the output signals, rapid eye movement (REM) sleep in the subject during the sleep session;

controlling the one or more sensory stimulators to deliver the sensory stimulation to the subject during the REM sleep to enhance the dream recall in the subject;

determining, based on the output signals, an electroencephalogram (EEG) for the subject during the sleep session;

determining a theta power for the EEG; and controlling the one or more sensory stimulators to deliver the sensory stimulation to the subject during the REM sleep to enhance the EEG theta power, the enhanced EEG theta power being associated with the dream recall in the subject, wherein controlling the one or more sensory stimulators to deliver the sensory stimulation to the subject during the REM sleep to enhance the EEG theta power comprises:

detecting, based on the output signals, a decrease in the EEG theta power associated with the subject during the REM sleep; and causing the one or more sensory stimulators to increase an intensity of the sensory stimulation delivered to the subject based on the detected decrease in the EEG theta power.

14. The method of claim 13, wherein the intensity of the sensory stimulation delivered to the subject is increased by a factor proportional to the decrease in the EEG theta power.

* * * * *